US006982361B1

(12) United States Patent
Raber et al.

(10) Patent No.: US 6,982,361 B1
(45) Date of Patent: Jan. 3, 2006

(54) METHOD OF SCREENING A COMPOUND FOR ANXIOLYTIC ACTIVITY IN AN APOLIPOPROTEIN E KNOCKOUT ANIMAL

(75) Inventors: Jacob Raber, San Francisco, CA (US); Lennart Mucke, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 633 days.

(21) Appl. No.: 09/512,840

(22) Filed: Feb. 25, 2000

(51) Int. Cl.
 *G01N 3/00* (2006.01)

(52) U.S. Cl. .............................. 800/3; 424/9.2; 800/13; 800/14; 800/18

(58) Field of Classification Search ................. 424/9.1, 424/9.2; 800/3, 8, 13, 14, 18
See application file for complete search history.

(56) References Cited

U.S. PATENT DOCUMENTS

| | | | | | |
|---|---|---|---|---|---|
| 5,145,866 | A | * | 9/1992 | Dunn et al. .................. | 514/425 |
| 5,767,337 | A | * | 6/1998 | Roses et al. .................... | 800/2 |
| 5,811,633 | A | * | 9/1998 | Wadsworth et al. ........... | 800/2 |
| 5,882,671 | A | * | 3/1999 | Helton et al. ................ | 424/456 |
| 6,046,381 | A | * | 4/2000 | Mucke et al. .................. | 800/18 |

OTHER PUBLICATIONS

Roses, AD. Apolipoprotein E in neurology. Curr Opin Neurol 9: 265–270, 1996.*
Polvikoski et al. Apolipoprotein E, dementia, and cortical deposition of beta–amyloid protein. N Engl J Med 333: 1242–1247, 1995.*
File et al. Striking changes in anxiety in Huntington's disease transgenic mice. Brain Research 805: 234–240, 1998.*
Orrell et al. Psychosocial stress and anxiety in senile dementia. J. Affective Disorders 39: 165–173, 1996.*
Cacabelos et al. APOE related frequency of cognitive and noncognitive symtoms in dementia. Meth Find Exp Clin Pharmacol 18(10): 693–706, 1996.*
Roses et al. ApoE, Alzheimer's disease, and recovery from brain stress. Annals NY Acad Sci 826: 200–212, 1997.*
Veinbergs et al. Differential neurotrophic effects of apolipoprotein E in aged transgenic mice. Neuroscience Letters 265: 218–222, 1999.*
Masliah et al. Neurodegeneration and cognitive impairment in apoE–deficient mice is ameliorated by infusion of recombinant apoE. Brain Research 751: 307–314, 1997.*

Raber et al. Differential effects of human apolipoprotein E isoforms on spatial learning/memory revealed in ApoE knockout mice. Society for Neurosci Abs 24(1–2): 736, 1998.*
Wozniak et al. ApoE4 transgenic male mice are profoundly impaired on the working memory protocol of the radial arm maze. Society for NeuroSci Abs 25(1–2): 55, 1999.*
Moechars et al. Expression in brain of amyloid precursor protein mutated in the alpha secretase site causes disturbed behavior, neuronal degeneration and premature death in transgenic mice. EMBO J. 15(6): 1265–1274, 1996.*
Stevenson et al. Phenotypic correction of hypercholesterolemia in ApoE–deficient mice by adenovirus–mediated in vivo gene transfer. Arterioscler Thromb Vasc Biol 15: 479–484, 1995.*
Chemerinski et al. Prevalence and correlates of anxiety in Alzheimer's disease. Depression and Anxiety 7: 166–170, 1998.*
Crawley, JN. Behavioral phenotyping of transgenic and knockout mice: experimental design and evaluation of general health, sensory functions, motors abilities, and specific behavioral tests. Brain Research 835: 18–26, 1999.*
Buttini et al. Expression of human Apolipoprotein E3 or E4 in the brains of ApoE–/– mice: isoform–specific effects on neurodegeneration. J. Neuroscience 19(12): 4867–4880, 1990.*
Pellow et al. Anxiolytic and anxiogenic drug effects on exploratory activity in an elevated plus–maze: a novel test of anxiety in the rat. Pharmacol. Biochem Behavior 24: 525–529, 1986.*
Raber, et al., "Isoform–specific effects of human apolipoprotein E on brain function revealed in ApoE knockout mice: Increased susceptibility of females", Proc. Natl. Acad. Sci USA., vol. 95, pp. 10914–10919, Sep. 1998.

* cited by examiner

*Primary Examiner*—Elizabeth Kemmerer
*Assistant Examiner*—Bridget E. Bunner
(74) *Attorney, Agent, or Firm*—Bret E. Field; Paula A. Borden; Bozicevic, Field & Francis, LLP (57) ABSTRACT

Methods and compositions for use in treating anxiety are provided. In the subject methods, an effective amount of an agent having ApoE3 activity is administered to a host suffering from an anxiety, e.g. excessive anxiety, unwanted anxiety, an anxiety disorder, etc. Also provided are methods and compositions for modulating adrenal steroidogenesis and/or release, particularly stress induced adrenal steroidogenesis and/or release, and the hippocampal-pituitary-adrenal (HPA) axis. In these methods, an effective amount of an ApoE activity modulating agent, e.g. an ApoE agonist or antagonist, is administered to the host.

13 Claims, 8 Drawing Sheets

METHOD OF SCREENING A COMPOUND FOR ANXIOLYTIC ACTIVITY IN AN APOLIPOPROTEIN E KNOCKOUT ANIMAL

FIELD OF THE INVENTION

The field of this invention is anxiety and the treatment thereof.

BACKGROUND OF THE INVENTION

Anxiety has been defined as excessive or inappropriate arousal characterized by feelings of apprehension, uncertainty, and fear. Often, there is no real or appropriate threat to which the anxiety can be attributed. Nevertheless, anxiety can paralyze an individual into inaction or withdrawal. Anxiety can also be a symptom of other psychologic or medical problems, such as depression, substance abuse, or thyroid disease.

Anxiety disorders are the most common psychiatric condition in the United States as about 25 million Americans experience anxiety disorders at some time during their lives. In recent years, a number of different anxiety disorders have been classified; the two primary ones are generalized anxiety disorder (GAD), which is long-lasting and low-grade, and panic disorder, which has more dramatic symptoms. Other anxiety disorders include phobias, performance anxiety, obsessive-compulsive disorder (OCD), and post-traumatic stress disorder (PTSD).

Although a number of different treatment protocols have been developed for use in the treatment of anxiety disorders, there is a continued interest in the development of new treatment methodologies and agents for use in treating these conditions.

RELEVANT LITERATURE

References of interest include: Cacabelos et al., Methods Find. Exp. Clin. Pharmacol. (December. 1996) 18:693–706; Gordon et al., Neurosci. Lett. (1996) 206:212–214; Nicosia et al., Mol. Endocrinol. (1992) 6:288–298; Prack et al., J. Lipid Res. (1991) 32:1611–1618; Zhou et al., Brain Res. (1998) 788:151–159.

SUMMARY OF THE INVENTION

Methods and compositions for use in treating anxiety are provided. In the subject methods, an effective amount of an agent having ApoE3 activity is administered to a host suffering from an anxiety, e.g. excessive anxiety, unwanted anxiety, an anxiety disorder, etc. Also provided are methods and compositions for modulating adrenal steroidogenesis and/or release, particularly stress induced adrenal steroidogenesis and/or release, and the hippocampal-pituitary-adrenal (HPA) axis. In these methods, an effective amount of an ApoE activity modulating agent, e.g. an ApoE agonist or antagonist, is administered to the host.

DESCRIPTION OF THE SPECIFIC EMBODIMENTS

Methods and compositions for use in treating anxiety are provided. In the subject methods, an effective amount of an agent having ApoE3 activity is administered to a host suffering from an anxiety, e.g. excessive anxiety, unwanted anxiety, an anxiety disorder, etc. Also provided are methods and compositions for modulating adrenal steroidogenesis and/or release, particularly stress induced adrenal steroidogenesis and/or release, and the hippocampal-pituitary-adrenal (HPA) axis. In these methods, an effective amount of an ApoE activity modulating agent, e.g. an ApoE agonist or antagonist, is administered to the host. In further describing the subject invention, the anxiety treatment methods and related methods and compositions will be described first, followed by a more in depth discussion of the adrenal steroidogenesis and/or release and HPA axis modulating methods and related methods and compositions of the subject invention.

Before the subject invention is further described, it is to be understood that the invention is not limited to the particular. embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Anxiety Treatment Methods

As summarized above, the subject invention provides methods and compositions for use in the treatment of anxiety, where the anxiety may or may not be due to an anxiety disorders. In other words, the subject invention provides, among other methods of treatment, a method for treating a host suffering from anxiety, including unwanted anxiety, excessive anxiety, anxiety disorders, etc. By anxiety is meant an apprehension of danger and dread accompanied by one or more of restlessness, tension, tachycardia, and dyspnea where the apprehension may or may not be attached to a clearly identifiable stimulus.

In treating a host suffering from anxiety according to the subject methods, an effective amount of an ApoE activity enhancing agent, and particularly an ApoE3 activity enhancing agent, is administered to the host. In other words, an effective amount of an ApoE agonist, and preferably an ApoE3 agonist, is administered to the host.

The term "ApoE agonist" is used broadly to refer to any agent that provides for increased ApoE activity in the host. As such, ApoE agonists include agents that provide for ApoE activity in a host initially devoid of ApoE activity, as well as agents that enhance or increase ApoE activity in a host initially exhibiting or having an initial amount of level of ApoE activity. Any convenient agent that provides for this increase in ApoE activity may be employed, where representative agents that may be used to provide for increased ApoE activity in the host include: ApoE or active fragments thereof, ApoE small molecule mimetics, nucleic. acids encoding products that exhibit ApoE activity, and the like. As mentioned above, of particular interest are ApoE3 agonists.

Isolated ApoE and/or active fragments and polypeptide analogues thereof, including recombinantly produced forms thereof, are described in U.S. Pat. Nos.: 5,672,685; 5,525, 472; 5,473,039; 5,182,364; 5,177,189; 5,168,045; 5,116, 739; the disclosures of which are herein incorporated by reference. ApoE3 is disclosed in Weisgraber, et al., "Human E apoprotein heterogeneity: cysteine-arginine interchanges in the amino acid sequence of the apo-E isoforms," J. Biol. Chem. (1981) 256: 9077–9083; and Rall, et al., "Structural basis for receptor binding heterogeneity of apolipoprotein E from type III hyperlipoproteinemic subjects," Proc. Nat. Acad. Sci. (1982) 79: 4696–4700. See also GenBank accession number K00396.

Where ApoE and ApoE3 small molecule mimetics are employed, a variety of different compounds are available. By small molecule is meant an agent that has a molecular weight that does not exceed about 10,000 daltons, usually 5,000 daltons and in many embodiments 2,500 daltons. Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Suitable small molecule agents can be identified using any convenient ApoE agonist activity screening assay, i.e. any convenient assay that is capable of providing information regarding -the ApoE activity of an agent. Of particular interest are ApoE3 small molecule mimetics that are capable of traversing the blood-brain barrier.

Nucleic acid encoding products that provide for the desired ApoE activity in the host may also be employed. Nucleic acids of interest are those that express ApoE or active: fragments thereof, as well as polypeptide analogues thereof and more particularly ApoE3 or active fragments or analogues thereof. Such genes are known to those of skill in the art. See e.g. U.S. Pat. Nos. 5,672,685; 5,525,472; 5,473, 039; 5,182,364; 5,177,189; 5,168,045; 5,116,739; the disclosures of which are herein incorporated by reference. See also GenBank accession no. K00396. Where nucleic acids are employed as the ApoE activity modulating agent, expression vectors may be used to introduce the gene into a target cell or tissue, e.g. adrenal cortex tissue. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. Where desired, means for providing at least one of temporal and spatial expression of the gene may be employed, where by temporal is meant time of expression and by spatial is meant location or tissue specificity of expression. For example, an inducible promoter may be included in the expression cassette which provides for expression of the encoded product at certain times, in response to the presence of certain stimuli, in certain specific tissues and cells, etc. Such promoters and methods for their use are well known to those of skill in the art. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks. The nucleic acid, e.g. gene, may be introduced into tissues or host cells by any number of routes, including viral infection, microinjection, or fusion of vesicles.

By treatment is meant that at least an amelioration of the symptoms associated with the anxiety affecting the host, where amelioration is used in a broad sense to refer to at least a reduction in the magnitude of a parameter, e.g. symptom, such as level or magnitude of apprehension, uncertainty, and fear, etc. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Also provided by the subject invention are methods for screening agents for anxiolytic activity, and particularly for ApoE3 anxiolytic activity. In these screening methods of the subject invention, a candidate anxiolytic agent is administered to an animal model of anxiety and the effect of the candidate compound on the anxiety in the animal model is determined and related to the anxiolytic properties of the candidate agent. A feature of the subject invention is that the anxiety animal model is generally an ApoE knockout mammal, e.g. an ApoE knockout mouse. By ApoE knockout animal model is meant an animal model that has been engineered to not express endogenous ApoE, e.g. a mouse model that does not express endogenous murine ApoE. ApoE knockout mice are known in the art and described in U.S. Pat. No. 5,767,337 as well as the patents and references cited therein, the disclosures of which are herein incorporated by reference. In these screening methods, the candidate agent in administered to the animal model and the animal model is then subjected to an anxiety measurement assay, e.g. the elevated plus maze, as described in the experimental section supra. The anxiety of the animal model in the assay is then determined and related to the anxiolytic activity of the candidate agent, e.g. through comparison with a control. When the animal model is a mouse model and the elevated plus maze is employed, an agent can be rapidly screened for anxiolytic activity, e.g. in less than 1 hour and usually less than .5 hours and often in as little as 10 mins or less, where one or more of the screening steps may be automated.

Also provided are methods for diagnosing a host with respect to an anxiety condition, e.g. whether a host is suffering from anxiety, whether a host is predisposed to suffer from anxiety and the like. In these diagnostic methods, the ApoE profile of the host is identified and related to anxiety or predisposition to anxiety in the host. In other words, the presence of, and in many embodiments relative amounts of, ApoE2, ApoE3 and ApoE4 are identified and related to anxiety or predisposition thereto in the host. For example, if a host lacks ApoE3, this indicates that the host is suffering from or may be predisposed to suffering from anxiety. Likewise, if host has elevated levels of ApoE4, this indicates that the host is suffering from or may be predisposed to anxiety.

Modulation of Adrenal Steroidogenesis and HPA Axis

As summarized above, the subject invention also provides methods and compositions for modulating steroidogenesis and/or steroid release in a host. As such, the subject invention provides methods for regulating steroid production and/or release in a host, i.e. methods of either increasing or decreasing steroid production and/or release in a host. More specifically, the subject methods are methods of modulating adrenal steroidogenesis and/or release, i.e. steroid production and/or release in the adrenal gland of a host. As such the subject methods are methods of modulating adrenal steroid hormone production and/or release, where the adrenal steroid hormone production and/or release is typically adrenal cortex steroid hormone production. Of particular interest in many embodiments is the regulation of adrenal glucocorticoid or GC production and/or release, e.g. adrenal corticosterone production. In many embodiments, the adrenal steroid production and/or release that is modulated by the subject methods is adrenal steroidogenesis in response to a CNS (central nervous system) induced stimulus, e.g. stress.

In other words, the subject methods in these embodiments are directed to methods of modulating adrenal steroidogenesis and/or release in response to stress signal originating in the CNS, e.g. brain.

Also provided by the subject invention are methods of modulating the HPA axis of a host, specifically to the extent that the HPA axis is under regulation of or is affected by adrenal steroid hormone production and release, particularly in response to a CNS stimulus, e.g. stress. The term modulating when used in connection with the HPA axis means changing the activity or function of the HPA axis. In other words, the subject methods provide a means for changing the nature of the chemical signals of the HPA axis such that physiological processes associated with HPA function are modulated or changed.

In practicing the subject methods, an effective amount of an ApoE activity modulating agent is administered to the host in a manner sufficient, e.g. in an amount effective, to at least modulate adrenal steroidogenesis and/or release in the host, and often to modulate HPA function in the host. By ApoE activity modulating agent is meant an agent that modulates or changes the overall ApoE activity in the host, particularly in the adrenal gland of the host and often in the adrenal cortex of the host. By ApoE activity is meant the physiological activity or properties of ApoE, e.g. biochemical interactions in which ApoE takes place. Thus, in certain embodiments the ApoE activity modulating agent is an agent that provides for increased ApoE activity in the host. In yet other embodiments, the ApoE activity modulating agent is an agent that provides for decreased ApoE activity in the host. Depending on whether increased or decreased ApoE activity is desired, a variety different ApoE activity modulating agents may be employed.

In those embodiments where it is desired to provide for increased ApoE activity in the host, e.g. to reduce adrenal steroidogenesis and/or modulate HPA activity through an increase an ApoE activity in the host, the ApoE activity modulating agent is an agent that provides for an increase in ApoE activity in the host. In other words, the ApoE activity modulating agent is an ApoE agonist. The term "ApoE agonist" is used broadly to refer to any agent that provides for increased ApoE activity in the host. As such, ApoE agonists include agents that provide for ApoE activity in a host initially devoid of ApoE activity, as well as agents that enhance or increase ApoE activity in a host initially exhibiting or having an initial amount of level of ApoE activity. Any convenient agent that provides for this increase in ApoE activity may be employed, where representative agents that may be used to provide for increased ApoE activity in the host include: ApoE or active fragments thereof, ApoE small molecule mimetics, nucleic acids encoding products that exhibit ApoE activity, and the like.

Isolated ApoE and/or active fragments and polypeptide analogues thereof, including recombinantly produced forms thereof, are described in U.S. Pat. Nos.: 5,672,685; 5,525,472; 5,473,039; 5,182,364; 5,177,189; 5,168,045; 5,116,739; the disclosures of which are herein incorporated by reference.

Where ApoE small molecule mimetics are employed, a variety of different compounds are available. By small molecule is meant an agent that has a molecular weight that does not exceed about 10,000 daltons, usually 5,000 daltons and in many embodiments 2,500 daltons. Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof Suitable small molecule agents can be identified using any convenient ApoE agonist activity screening assay, i.e. any convenient assay that is capable of providing information regarding the ApoE activity of an agent.

Nucleic acid encoding products that provide for the desired ApoE activity in the host may also be employed. Nucleic acids of interest are those that express ApoE or active fragments thereof, as well as polypeptide analogues thereof. Such genes are known to those of skill in the art. See e.g. U.S. Pat. Nos. 5,672,685; 5,525,472; 5,473,039; 5,182,364; 5,177,189; 5,168,045; 5,116,739; the disclosures of which are herein incorporated by reference. Where nucleic acids are employed as the ApoE activity modulating agent, expression vectors may be used to introduce the gene into a target cell or tissue, e.g. adrenal cortex tissue. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. As mentioned above, means for controlling expression in a spatial and/or temporal manner may be included in the transcription cassette. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks. The nucleic acid, e.g. gene, may be introduced into tissues or host cells by any number of routes, including viral infection, microinjection, or fusion of vesicles.

In those embodiments where it is desired to provide for decreased ApoE activity in the host, e.g. to increase adrenal steroidogenesis and/or modulate HPA activity through a decrease in ApoE activity in the host, the ApoE activity modulating agent is an agent that provides for a decrease in ApoE activity in the host. In other words, the ApoE activity modulating agent is an ApoE antagonist. The term "ApoE antagonist" is used broadly to refer to any agent that provides for decreased ApoE activity in the host. As such, ApoE antagonists include agents that provide for reduced or decreased ApoE activity in a host initially exhibiting or having an initial amount of level of ApoE activity. Any convenient agent that provides for this decrease in ApoE activity may be employed, where representative agents that may be used to provide for decreased ApoE activity in the host include: small and large molecule antagonist compounds, nucleic acids that inhibit ApoE expression, and the like. As such, small molecule compounds such as those described above that exhibit ApoE antagonist activity in ApoE. activity screening assays may be employed. Large molecule antagonist compounds of interest include protein and polypeptides, as well as fragments or analogues thereof, that decrease the endogenous ApoE activity in the host, e.g. by interfering with ApoE binding to its target(s) in the host.

Nucleic acids of interest for use in providing for decreased ApoE activity in the host include antisense molecules. Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are select for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434–42). Examples of oligonucleotides with catalytic activity are described in WO 9506764. Conjugates of anti-sense ODN with a metal complex, e.g. capable of mediating mRNA hydrolysis are described in Bashkin et al. (1995), *Appl. Biochem. Biotechnol.* 54:43–56.

As mentioned above, in the subject methods of modulating adrenal steroidogenesis and the HPA axis, an effective amount of the ApoE activity modulating agent is administered to the host. In this specification "effective amount" means a dosage sufficient to produce a desired result, where the desired result in the desired increase or decrease in ApoE activity in the host and concomitant modulation of steroidogenesis and HPA axis activity. The actual amount that is the effective amount varies depending on the specific nature of the active agent, but may be determined empirically by those of skill in the art.

The above described methods find use in a variety of applications, including the treatment of disease conditions associated with adrenal steroidogenesis and HPA axis activity. As such, the subject methods find use in the treatment of disease conditions associated with abnormalities in cognition, emotion or feeding. Specific disease conditions associated with cognition and treatable according to the subject methods include: Alzheimer's disease, AIDS dimentia, Cushing's disease, depression; and the like. Specific disease conditions associated with emotion and treatable according to the subject methods include: anxiety disorders and the like. Specific disease conditions associated with feeding and treatable according to the subject methods include: obesity, and the like.

By treatment is meant that at least an amelioration of the symptoms associated with the condition afflicting the host, where amelioration is used in a broad sense to refer to at least a reduction in the magnitude of a parameter, e.g. symptom (such as level of anxiety, degree of obesity, etc.), associated with the condition being treated, etc. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are-within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Administration of Active Agents

In the above described methods, the active agent(s) may be administered to the host using any convenient means. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal,etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene. glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In certain embodiments, lipid containing delivery vehicles are of interest in the administration of subject agents.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Kits

Also provide are kits for practicing the subject methods. Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

The following examples are offered by way of illustration and not by way of limitation.

EXPERIMENTAL

I. Anxiety Assays

A. Materials and Methods

Animals. Male $Apoe^{-/-}$ (C57BL/6J-Apoe$^{tm1\ Unc}$) and wild-type C57BL/6J mice were obtained from Jackson Laboratories (Bar Harbor, Me.). Male and female $Apoe^{-/-}$ mice expressing human ApoE3; human ApoE4; and human ApoE3 and ApoE4 were the same as those described in Raber et al, P.N.A.S. USA (Sep. 1, 1998) 95:10914–10919 and Buttini et al., J. Neurosci. (Jun. 15, 1999) 19: 4867–4880.

Elevated plus maze. Anxiety levels were assessed with an elevated, plus-shaped maze consisting of two open arms and two closed arms equipped with rows of infrared photocells interfaced with a computer (Hamilton, Poway, Calif.). Mice were placed individually in the center of the maze and allowed free access for 10 min. They could spend their time either in a closed safe area (closed arms) or in an open area (open arms). Recorded beam brakes were used to calculate the time spent in the open arms, the distance moved in the open arms, and the number of times the mice extended over the edges of the open arms. Reductions in these variables indicate increased anxiety. After behavioral testing, the equipment was cleaned with 1 mM acetic acid to remove odors.

B. Results

Figure 1:
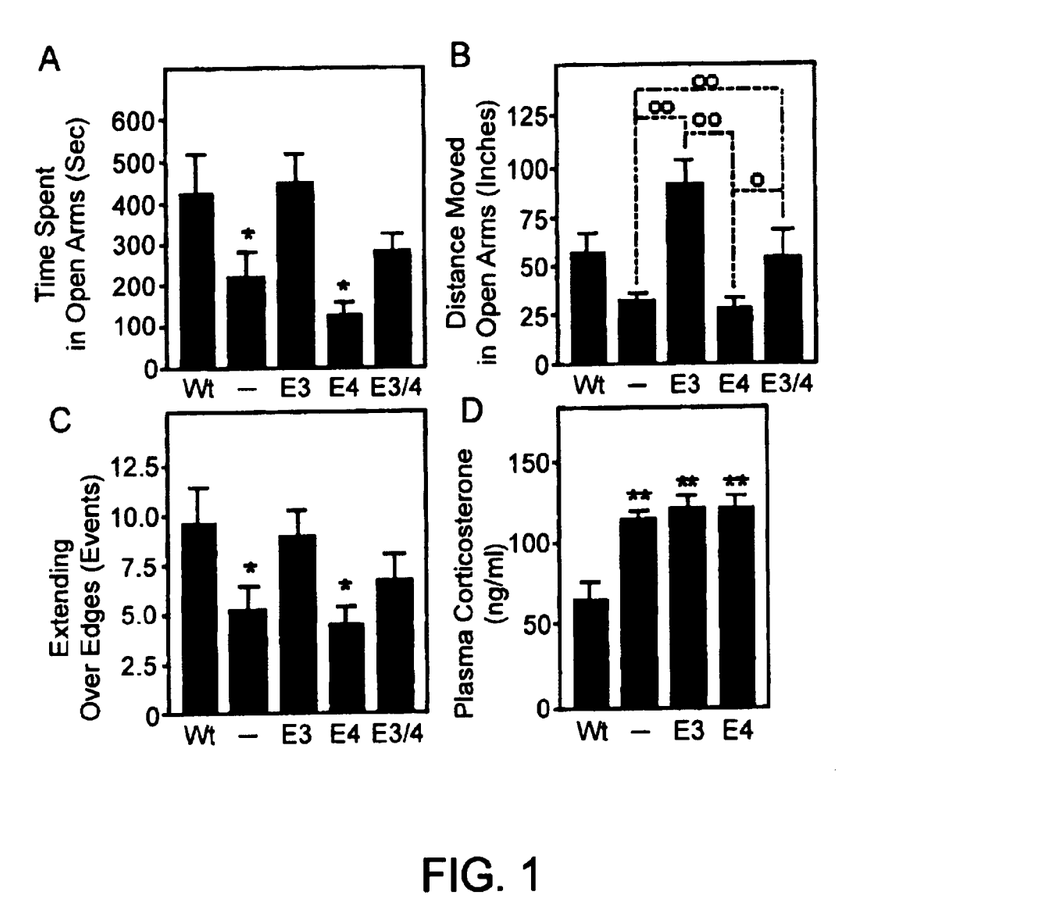
FIGS. 1A–1D and FIG. 2 provide graphical tests of the results from elevated plus maze testing of Wildtype, ApoE –/–, ApoE –/– mice expressing ApoE3, ApoE –/– mice expressing ApoE4 and ApoE –/– mice expressing ApoE3 and ApoE4.
Figure 2:
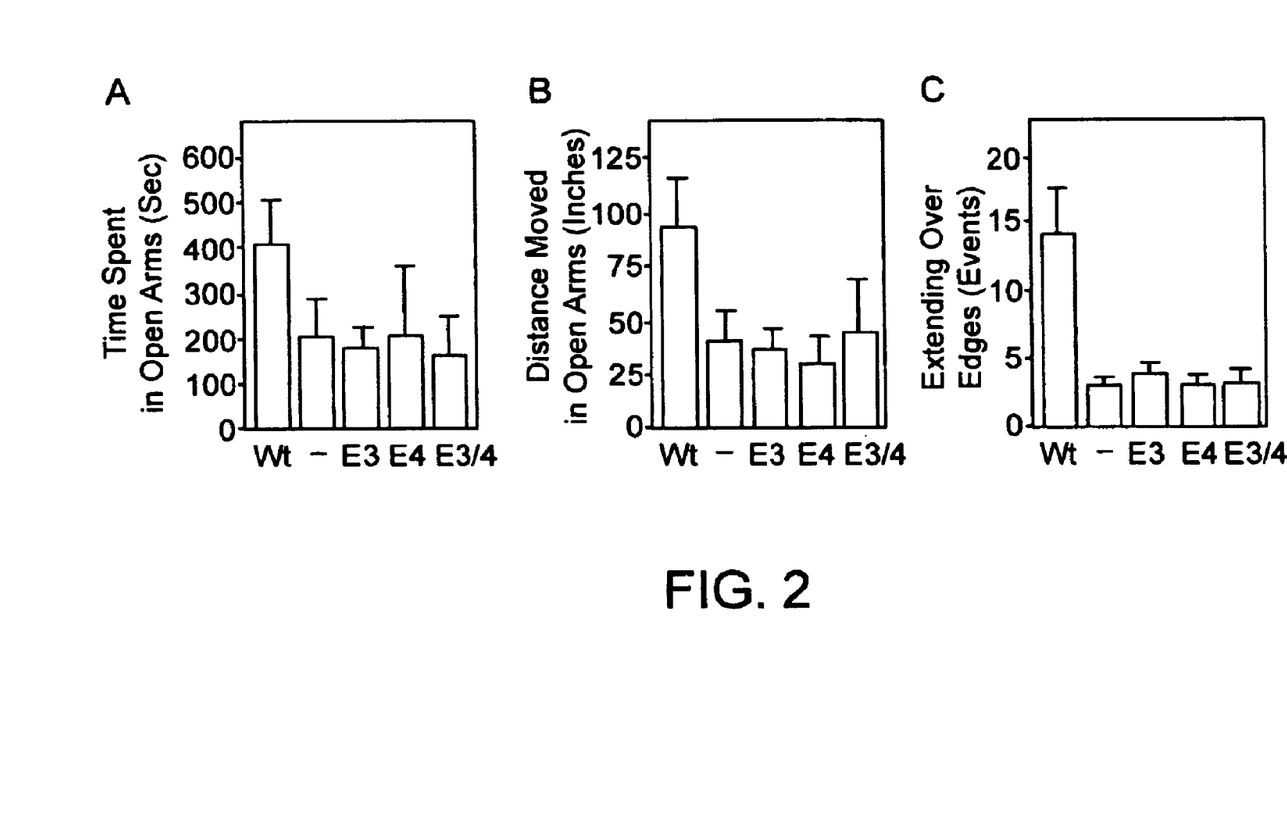

Wildtype, ApoE –/–, ApoE –/– mice expressing ApoE3, ApoE –/– mice expressing ApoE4 and ApoE –/– mice expressing ApoE3 and ApoE4 were tested in the elevated plus maze as described above. The results are provided graphically in FIGS. 1 to 2.

C. Discussion

The above results demonstrate that ApoE knockout mice show increased anxiety, and that neuronal expression of ApoE3, but not of ApoE4, prevents this increased anxiety in male, but not in female, mice. The elevated plus maze also revealed that ApoE knockout male mice expressing both ApoE3 and ApoE4 in neurons show anxiety levels intermediate between the anxiety levels observed in ApoE knockout male mice expressing ApoE3 or ApoE4 alone. In contrast, ApoE knockout female mice expressing both ApoE3 and ApoE4 in neurons show anxiety levels similar to those observed in ApoE knockout female mice.

The above results demonstrate that ApoE3 has anxiolytic properties and therefore ApoE3 or agonist mimetics thereof are useful in treating anxiety disorders. The above results also demonstrate that the above described animal models are useful to test the efficacy of anxiolytic drugs and to assess whether drugs enhance or inhibit apoE3-like or ApoE4-like effects on the hypothalamic-pituitary-adrenal axis and emotional responses.

II. Adrenal Steroidogenesis and HPA Axis Assays

A. Materials and Methods

Animals. Male Apoe (C57BL/6J-Apoe$^{tm1\ Unc}$) and wild-type C57BL/6J mice were obtained from Jackson Laboratories (Bar Harbor, Me.). Mice were housed under conditions of constant temperature (18° C.), light from 6:00 a.m. to 6:00 p.m., and access to food and water ad libitum. To avoid circadian variation, they were tested or killed between 10:00 a.m. and 12:00 noon, unless indicated otherwise. To minimize the effects of social influences on behavior, mice were housed individually for 7 days before assessment of open field activity or plus maze performance (see below). Mice were also housed individually for measurements of food and water intake. Otherwise, they were group housed.

Open field activity. Mice were placed individually into brightly lit automated activity cages equipped with rows of infrared photocells interfaced with a computer (San Diego Instruments, San Diego, Calif.). After a 1-min adaptation period, open field activity was recorded for 10 min on 3 consecutive days. Recorded beam breaks were used to calculate active times, path lengths, rearing times, and rearing events. After behavioral testing, the equipment was cleaned with 1 mM acetic acid to remove odors.

Elevated plus maze. Anxiety levels were assessed with an elevated, plus-shaped maze consisting of two open arms and two closed arms equipped with rows of infrared photocells interfaced with a computer (Hamilton, Poway, Calif.). Mice were placed individually in the center of the maze and allowed free access for 10 min. They could spend their time either in a closed safe area (closed arms) or in an open area (open arms). Recorded beam brakes were used to calculate the time spent in the open arms, the distance moved in the open arms, and the number of times the mice extended over the edges of the open arms. Reductions in these variables indicate increased anxiety. After behavioral testing, the equipment was cleaned with I mM acetic acid to remove odors.

Corticosterone and ACTH measurements. To determine plasma corticosterone and adrenocorticotropin (ACTH) levels, adrenal corticosterone or pituitary ACTH content, mice were anesthetized with metofane for 2 min, decapitated, and bled into EDTA-containing tubes (Microtainer, Becton-Dickinson, Rutherford, N.J.), and the adrenal glands and pituitaries were removed and placed on dry ice until extraction and assay for corticosterone or ACTH as described below. The same group of mice was used to determine basal plasma corticosterone and ACTH levels and adrenal corticosterone content. The blood was spun at 10,000×g for 10 min at 4° C., and the supernatant was stored at −70° C. until assayed for corticosterone or ACTH. Corticosterone was measured with a corticosterone RIA kit for rats and mice (ICN Biomedicals, Costa Mesa, Calif.). The intra- and interassay coefficients of variation were both 7%. ACTH was measured with an ACTH RIA kit (Nichols Institute, Capistrano, Calif.). The intra- and interassay coefficients of variation were 3% and 7%, respectively.

Adrenal corticosterone extraction. To extract corticosterone, the adrenals were homogenized in 5 ml of 0.1 M phosphate-buffered saline, pH 7.4, with a polytron (Virtis, Gardiner, N.Y.). After the addition of 5 ml of isooctane and 5 ml of ethylacetate, the samples were vortexed for 5–8 min with a multitube vortexer and centrifuged at 4,000 rpm for 5 min in an Omnifuge RT. The upper organic phase was extracted according to the protocol of Mellon (1980), as modified by Akwa et al. (1993). The extraction procedure was repeated twice, and the organic phase was evaporated under a stream of nitrogen gas at 60° C. The pellets were resuspended in 400 l of methanol and 600 l of steroid diluent (ICN Biomedicals, Costa Mesa, CA) and stored in the dark at 4° C. until assayed for corticosterone.

Pituitary ACTH extraction. To extract ACTH, pituitary samples were placed in 500 l of 2N acetic acid, boiled for 10 min, cooled on ice, and sonicated twice for 3 sec with a Vir Sonic 50 sonicator (Virtis, Gardiner, N.Y.). After centrifugation at 10,000×g for 10 min and removal of an aliquot for protein determination (Micro BCA* protein assay reagent kit, Pierce, Rockford, Ill.), samples containing 450 l were lyophilized overnight (Freeze Mobile 5SL, Virtis, Gardiner, N.Y.). The lyophilized samples were resuspended in 450 $\mu$l of radioimmunoassay (RIA) buffer (Raber et al., 1997) and stored at −70° C. until assayed for ACTH immunoreactivity.

ACTH challenge and urinary corticosterone measurements. To determine adrenal sensitivity, naïve mice were individually housed in metabolic cages, as described Akana, Endocr. Soc. Abstr. (1999) V139A:364. After 1 week of habituation to the cages, urine was collected from 5:00 p.m. to 7:00 a.m. and from 7:00 a.m. to 5:00 p.m. for 7 consecutive days. After the 5:00 p.m. collection, the mice were challenged with saline (0.1 ml/mouse, i.p.) on the second and fourth days, and with highly purified ACTH (ACTHar) (0.4 U/mouse, 0.1 ml, i.p.) (Rhone-Poulenc Rorer Pharmaceutical Inc of Collegeville, Pa. 19426) on the seventh day. The volume of the urine samples was recorded, and the samples were stored at 4° C. until assayed for corticosterone.

Adrenal histology. For histological and lipid analysis, adrenal glands were removed from decapitated Apoe$^{-/-}$ and wild-type mice, fixed in formalin, and embedded in paraffin. Sections (5 $\mu$m) were stained with hematoxylin and eosin and brightfield photographs were taken on a Leica microscope. Alternatively, sections were stained with Nile Red (9-diethylamino-5H-benzo [$\alpha$] phenoxazine-5-one) to identify lipid deposits and viewed with a MRC-1024 laser scanning confocal microscope (Bio-Rad, Hercules, Calif.) mounted on an Optiphot-2 microscope (Nikon, Tokyo, Japan).

Dissection of adipose tissues and plasma leptin measurements. Mice were killed by decapitation. Epididymal white adipose tissue (around the testis), mesenteric white adipose tissue (around the stomach), and interscapular brown adipose tissue were dissected. Landmarks for dissection of white adipose tissue depots followed the planes of the tissue fascia capsule. Epididymal white adipose tissue included the fat pad surrounding the testis and was dissected free of the spermatic cord, testis, and epididymis. Mesenteric fat included all the fascia enclosed fat and minor blood vessels surrounding the gastrointestinal tract and excluded the pancreas and major lymph nodes. Plasma leptin levels were measured with a leptin RIA (Linco, St. Charles, Mo.). The intra- and interassay coefficients of variation were 3% and 10%, respectively.

Food and water intake. Naïve mice were housed individually. The food and water intake of mice over 5 consecutive days was measured by weighing the remaining food and water.

Statistical analysis. Data are expressed as mean±SEM. The statistical significance of differences between aged-matched groups was determined by ANOVA followed by Tukey-Kramer test when appropriate. p<0.05 was considered significant.

B. Results

Plasma Corticosterone Levels of Apoe$^{-/-}$ and Wild-type Mice

Figure 3:
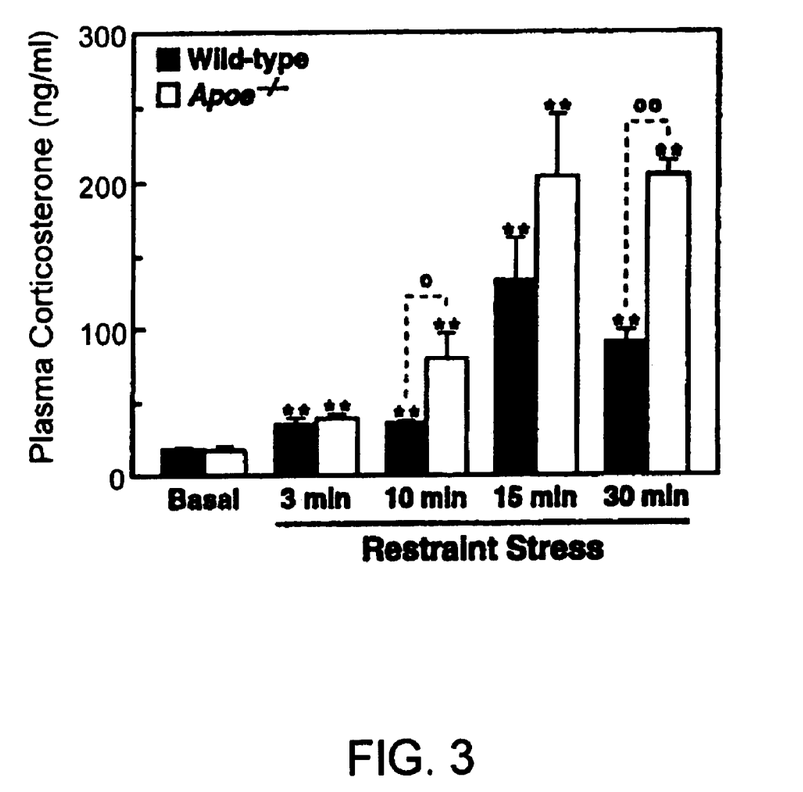
FIG. 3. Plasma corticosterone levels in 6-month-old Apoe$^{-/-}$ and wild-type mice at baseline (basal) and after 3, 10, 15, or 30 min of restraint stress. The same mice were used to determine basal plasma ACTH levels (FIG. 2), adrenal corticosterone content (Table 1), and pituitary ACTH content (see text). **$p<0.01$ versus basal; $^{0}p<0.05$; $^{00}p<0.01$; n=4–9 mice/group.

At 3 months of age, there was no significant difference in basal plasma corticosterone levels between Apoe$^{-/-}$ mice and wild-type controls (30.2±6.8 ng/ml and 23.7±4.6 ng/ml, respectively, n=4 mice/group). Ten minutes of restraint stress is a sensitive procedure to assess HPA axis responsivity (Raber et al., J. Neurosci. (1997)17:9473–9480). After 10 min of restraint stress, plasma corticosterone levels increased markedly, but there was no difference in plasma corticosterone levels between the Apoe$^{-/-}$ (140.5±22.2 ng/ml ) and wild-type (140.7±6.2 ng/ml) mice at 3 months of age (n=5 mice/group). In contrast, 6-month-old Apoe$^{-/-}$ mice had significantly higher plasma corticosterone levels than wild-type mice after 10 min and 30 min of restraint stress (FIG. 3). Under basal conditions and after 3 min of restraint stress, Apoe$^{-/-}$ mice and wild-type controls had similar plasma corticosterone levels. A difference in plasma corticosterone levels after 10 min of restraint stress between Apoe$^{-/-}$ (109.1±35.9 ng/ml) and wild-type (66.8±8.0 ng/ml) mice was also detected at 18 months of age (n=4 mice/group).

There were no significant differences in basal plasma corticosterone levels between wild-type and Apoe$^{-/-}$ mice in the late afternoon, when plasma corticosterone levels in rodents normally peak (Dailman et al., 1987), although there was a trend toward higher basal corticosterone levels in Apoe$^{-/-}$ (68.9±13.3 ng/ml) than in wild-type (41.2±10.3 ng/ml) mice (n=4 mice/group).

Adrenal Corticosterone Content and Histology

The adrenal corticosterone content was similar in Apoe$^{-/-}$ and wild-type mice at 3 months of age, but was significantly higher in Apoe$^{-/-}$ mice than in wild-type mice at 6 months of age (Table 1).

TABLE 1

Adrenal corticosterone content in Apoe$^{-/-}$ and wild-type mice

| Group | Adrenal Weight mg | Corticosterone content ng/gland | ng/mg protein |
|---|---|---|---|
| 3-Month-Old Mice | | | |
| Wild-type (n = 5) | 10.8 ± 1.3 | 32.6 ± 6.1 | 2.9 ± 0.4 |
| Apoe$^{-/-}$ (n = 5) | 10.3 ± 0.7 | 32.6 ± 5.8 | 3.3 ± 0.6 |
| 6-Month-Old Mice | | | |
| Wild-type (n = 9) | 10.8 ± 1.1 | 31.2 ± 6.1 | 2.9 ± 0.1 |
| Apoe$^{-/-}$ (n = 9) | 14.4 ± 1.6 | 74.0 ± 12.8* | 5.9 ± 1.5 |

*p < 0.01 versus age-matched wild-type mice (Tukey-Kramer test). The same groups of mice were used to determine basal plasma corticosterone levels (see FIG. 3 and text).

This difference in adrenal corticosterone content is consistent with the increased plasma corticosterone after restraint stress in 6-month-old Apoe$^{-/-}$ mice. The adrenal glands in both 6-month-old groups showed similar hematoxylin and eosin staining (data not shown). However, 6-month-old Apoe$^{-/-}$ mice showed increases in lipid droplets in both the adrenal cortex and the medulla, consistent with hypersecretion of adrenal corticosterone and increased adrenal corticosterone content (Hall and Almahbobi, Microscopy Res. Techniques (1997) 36:463–479).

Plasma and Pituitary ACTH Levels

To determine the role of central HPA alterations in the stress-induced plasma corticosterone elevations of Apoe$^{-/-}$ mice, plasma and pituitary ACTH levels were analyzed. At 3 months of age, there was no significant difference in basal ACTH levels between Apoe$^{-/-}$ (65.8±11.8 pg/ml) and wild-type (60.2±5.3 pg/mi) mice (n=4 mice/group). After 10 min of restraint stress, plasma ACTH levels increased markedly, but there was no significant difference in plasma ACTH levels between Apoe$^{-/-}$ (362.2.8±42.8 pg/ml) and wild-type (273.3±48.9 pg/ml) mice (n=5 mice/group; p=0.096).

Figure 4:
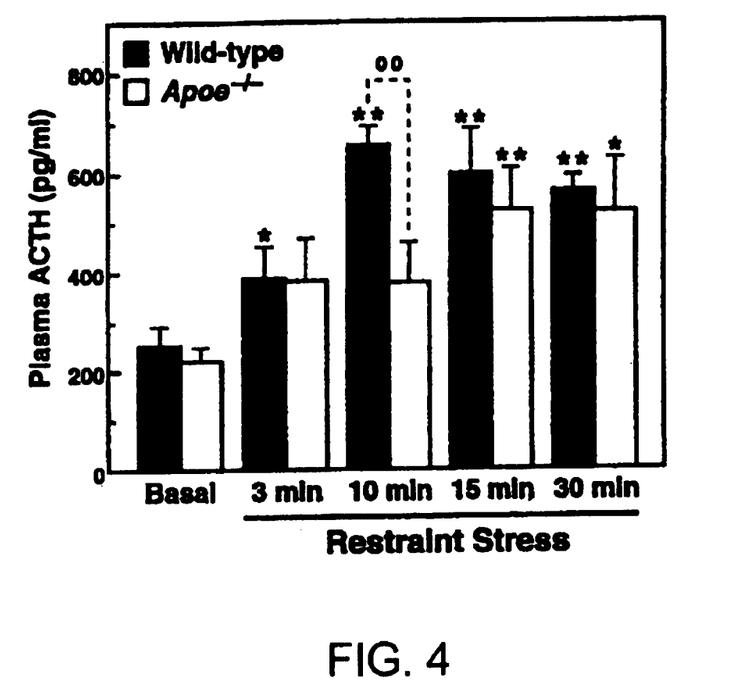
FIG. 4. Plasma ACTH levels in 6-month-old wild-type and Apoe$^{-/-}$ mice at baseline (basal) and after 3, 10, 15, and 30 min of restraint stress. *$p<0.05$, **$p<0.01$ versus basal; $^{00}p<0.01$; n=4–9 mice/group.

There was also no significant difference in basal plasma ACTH levels between 6-month-old Apoe$^{-/-}$ and wild-type mice (FIG. 4). However, restraint stress-induced ACTH levels in 6-month-old Apoe$^{-/-}$ mice were disproportionally low (FIG. 4) compared to the increased stress-induced plasma corticosterone levels observed at this age (FIG. 3). There were no significant differences in pituitary ACTH content between Apoe$^{-/-}$ (0.243±0.088 pg/μg protein, n=5) and wild-type (0.205±0.032 pg/μg protein, n=9) mice.

Adrenal Sensitivity to ACTH Challenge

Figure 5:
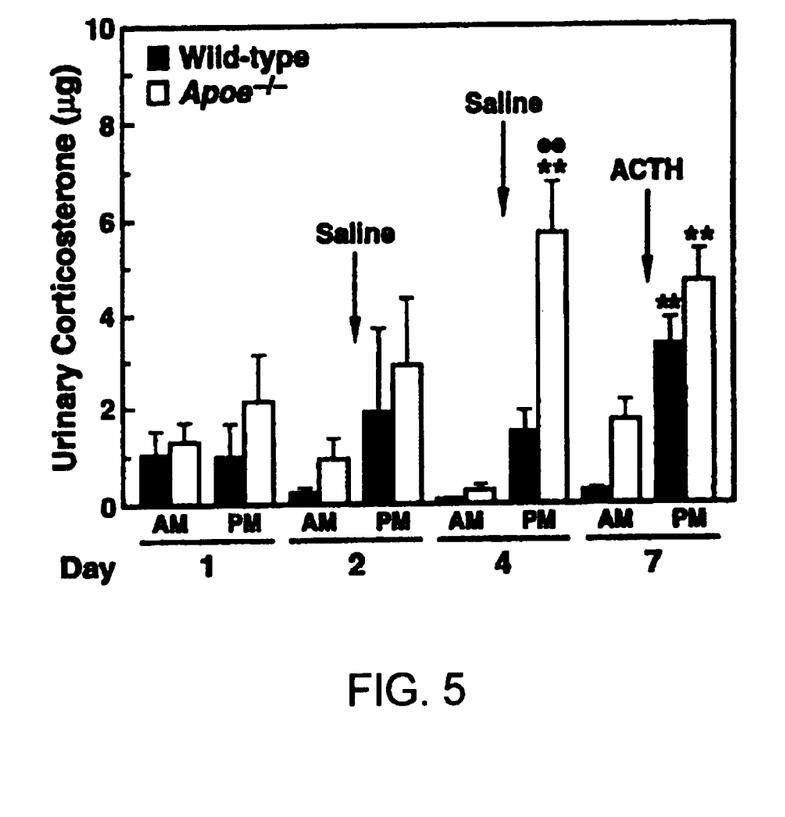
FIG. 5. Adrenal responsivity to ACTH challenge 6-month-old Apoe$^{-/-}$ and wild-type mice. Naive mice were housed in metabolic cages. After 1 week of habituation to the novel environment, urine was collected from 5:00 p.m. to 7:00 a.m. (PM bars) and from 7:00 a.m. to 5:00 p.m. (AM bars). After the 5:00 p.m. collection, mice were challenged with saline (0.1 ml/mouse, i.p.) on the second and fourth days and with 0.4 U of ACTHar (0.1 cc/mouse, i.p.) on the seventh day. **$p<0.01$ versus a.m.; ¨$p<0.01$ versus wild-type; n=6–7 mice/group.

A higher sensitivity of the adrenal gland of Apoe$^{-/-}$ mice to stimulation with ACTH might explain the relatively low plasma ACTH levels and high plasma corticosterone levels after restraint stress (FIGS. 3 and 4). To test this possibility, we used metabolic cages to measure overnight urinary corticosterone excretion in 6-month-old Apoe$^{-/-}$ and wild-type mice challenged at 5:00 p.m. with saline or highly purified ACTH (ACTHar) (FIG. 5). After the second saline injection, the plasma urinary corticosterone excretion increased more in Apoe$^{-/-}$ mice than in wild-type mice (p<0.01). However, there was no significant difference in the ACTHar-induced corticosterone levels between the two groups. When challenged with 0.2 or 2.0 U of ACTHar, Apoe$^{-/-}$ and wild-type mice also showed a similar adrenal sensitivity (data not shown). Thus, Apoe$^{-/-}$ mice did not exhibit an increased adrenal sensitivity to ACTH.

Behavioral Alterations in Apoe$^{-/-}$ Mice

Figure 6:
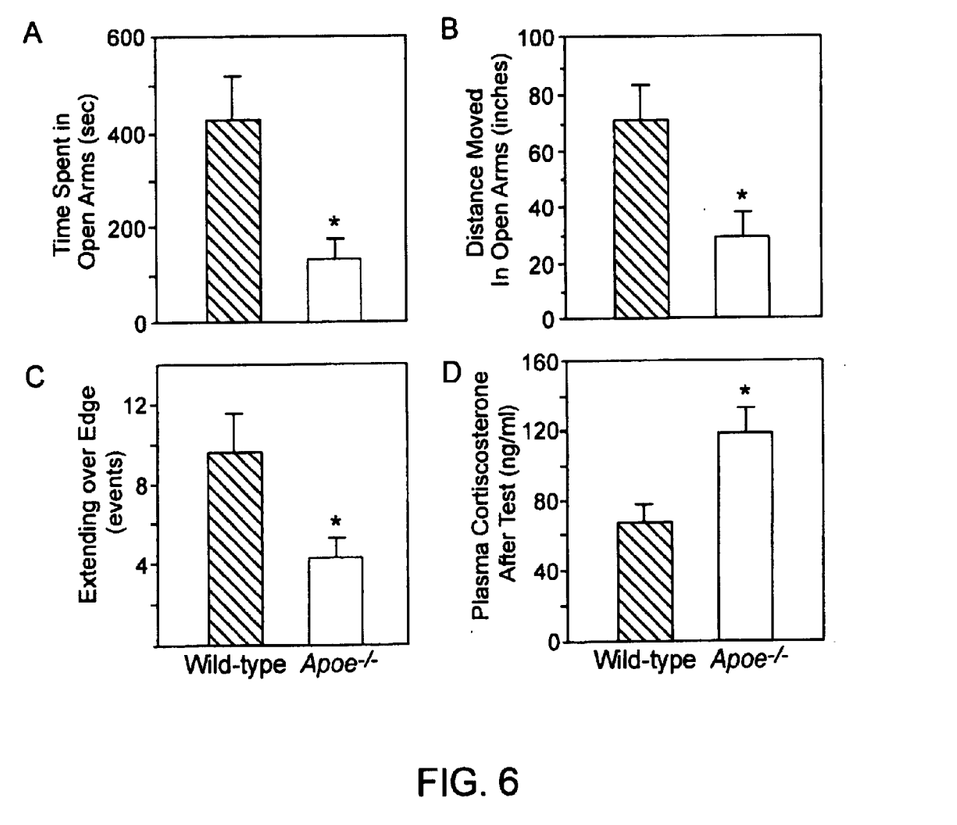
FIG. 6. Anxiety levels in 6-month-old Apoe$^{-/-}$ and wild-type mice assessed in the elevated plus maze. Compared with the wild-type controls, Apoe$^{-/-}$ mice showed reductions in the time spent in the open arms (A), in the distance moved in the open arms (B), and in the number of times they extended over the edges of the open arms to explore (C). Apoe$^{-/-}$ mice also. had abnormally increased plasma corticosterone levels after behavioral testing (D), consistent with increased anxiety. *$p<0.05$ versus wild-type; n=8 mice/group.

We next determined possible behavioral consequences of HPA axis dysregulation in Apoe$^{-/-}$ mice. When anxiety levels were assessed in the elevated plus maze, 6-month-old male Apoe$^{-/-}$ mice showed more anxiety than wild-type controls (FIGS. 6A-C). Apoe$^{-/-}$ mice also had higher plasma corticosterone levels than wild-type controls after behavioral testing (FIG. 6D). However, no significant differences in horizontal or vertical exploratory activity were detected between these groups of mice in the open field (Raber et al., 1998). In contrast, at 12 months of age, exposure to a novel open field elicited significantly less horizontal and vertical activity in Apoe$^{-/-}$ mice than in wild-type controls (FIG. 7).

Figure 7:
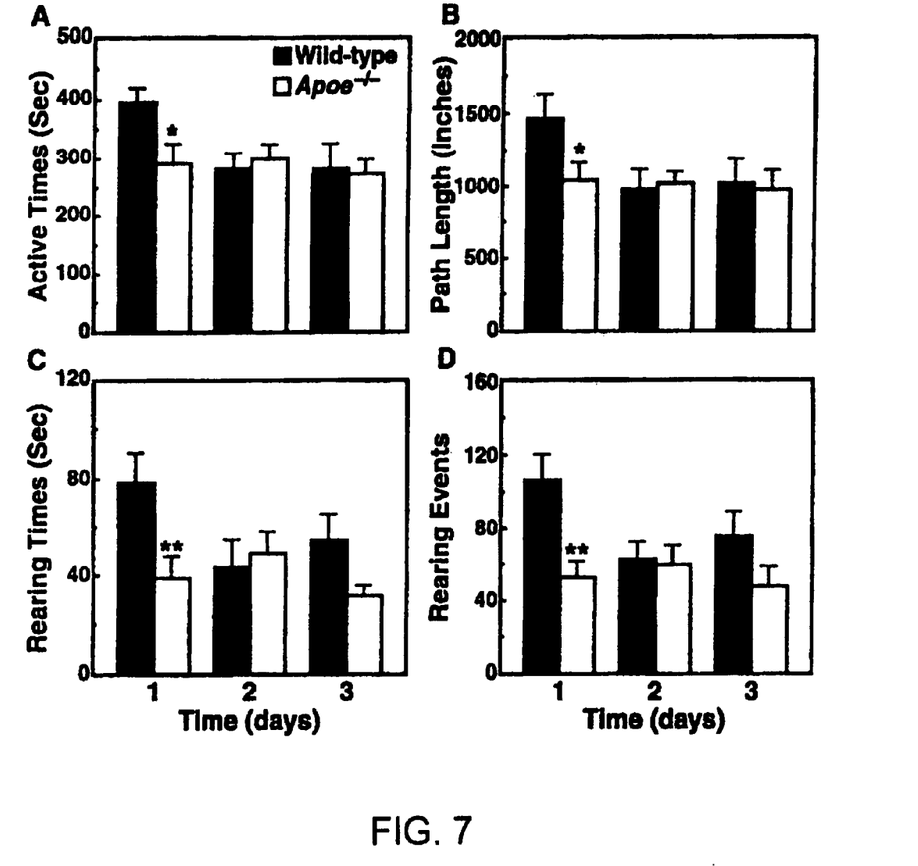
FIG. 7. Open field activity of 12-month-old Apoe$^{-/-}$ and wild-type mice. On each of 3 consecutive days, open field activity was recorded after an initial 1-min adaptation period. In wild-type mice, horizontal and vertical activities declined significantly ($p<0.01$, ANOVA). On day 1, the active times (A), path lengths (B), and the frequency (C) and duration (D) of rearing events were significantly reduced in Apoe$^{-/-}$ mice compared with wild-type controls. Apoe$^{-/-}$ mice showed no further decline in horizontal or vertical activity on days 2 or 3. *$p<0.05$, **$p<0.01$ versus wild-type; Tukey-Kramer test; n=8 mice/group.

On subsequent days, Apoe$^{-/-}$ mice showed no decline in exploratory activity, whereas age-matched wild-type mice showed a significant decrease in horizontal and vertical activity between days 1 and 2 (p<0.01) (FIG. 7).

Metabolic Alterations in Apoe$^{-/-}$ Mice

Figure 8:
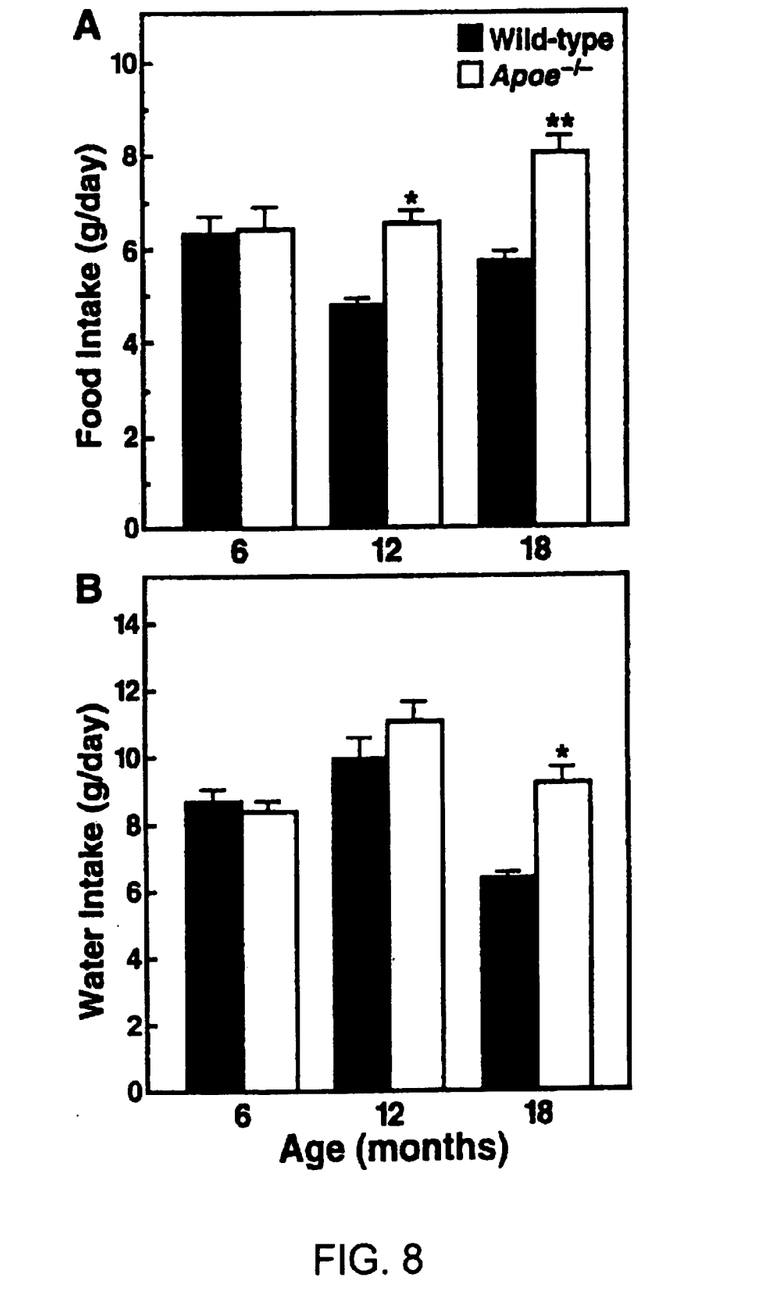
FIG. 8. Food (A) and water (B) intake of 6-, 12-, and 18-month-old Apoe$^{-/-}$ and wild-type mice was measured over 5. consecutive days and averaged. *$p<0.05$, **$p<0.01$ versus wild-type; n=5–11 mice/group.

Since the HPA axis is involved in regulating energy balance (Akana et al., Endocrinology (1994) 135:1125–1134; Dallman et al., Ann. N.Y. Acad. Sci. (1994) 746:22–32), the possibility of whether the HPA axis dysregulation might be associated with metabolic alterations in Apoe$^{-/-}$ mice was examined. Food and water intake was compared in Apoe$^{-/-}$ mice and wild-type controls (FIG. 8). At 6 months of age, there were no differences between Apoe$^{-/-}$ mice and wild-type controls. However, Apoe$^{-/-}$ mice showed significant increases in food intake at 12 and 18 months of age and in water intake at 18 months of age (FIG. 8).

Next an analysis was made to determine whether the increased energy intake in Apoe$^{-/-}$ mice was associated with other metabolic alterations (Table 2).

TABLE 2

Metabolic characteristics of Apoe$^{-/-}$ mice

| Characteristic | 6-Month-Old | | 18-Month-Old | |
| --- | --- | --- | --- | --- |
| | Wild-type | Apoe$^{-/-}$ | Wild-type | Apoe$^{-/-}$ |
| Body weight (g) | 33.9 ± 0.8 | 33.2 ± 2.0 | 31.2 ± 1.0 | 41.5 ± 3.7* |
| Stomach[1] | 172.8 ± 20.0 | 229.6 ± 33.2 | 205.5 ± 7.1 | 286.3 ± 44.2* |
| Adipose Tissues[1] | | | | |
| Interscapular brown | 33.6 ± 0.3 | 30.7 ± 1.2 | 38.0 ± 3.8 | 24.2 ± 0.4* |
| Mesenteric white | 161.7 ± 15.6 | 108.4 ± 19.1 | 226.1 ± 14.2 | 197.4 ± 19.2 |
| Epididymal white | 141.8 ± 15.6 | 59.3 ± 4.7** | 105.0 ± 10.4 | 74.0 ± 8.3* |
| Leptin (ng/ml) | 6.3 ± 0.9 | 1.7 ± 0.5 | 4.3 ± 0.8 | 2.6 ± 0.6* | n = 4–8 mice/group
[1]Values represent mg/10 g body weight to correct for differences in body weight.
*p < 0.05,
**p < 0.01 versus wild-type (Tukey-Kramer test).

Compared with age-matched wild-type mice, Apoe$^{-/-}$ mice showed significant increases in stomach and body weight and decreases in interscapular brown adipose tissue at 18, but not at 6, months of age. Plasma leptin levels and epididymal white adipose tissue were significantly lower in Apoe$^{-/-}$ mice than wild-type controls at both 6 and 18 months of age.

C. Discussion

This above results demonstrate that apoE deficiency in mice results in an age-dependent dysregulation of the HPA axis through a mechanism affecting primarily the adrenal gland. Apoe$^{-/-}$ mice had an age-dependent increase in adrenal corticosterone content at baseline and abnormally increased plasma corticosterone levels after restraint stress, whereas their plasma and pituitary ACTH levels were either unchanged or decreased compared with those in wild-type controls. The dysregulation of the HPA axis in Apoe$^{-/-}$ mice was associated with behavioral and metabolic alterations. The above described findings with respect to increased adrenal corticosterone content and stress-induced corticosterone hypersecretion in Apoe$^{-/-}$ mice demonstrate that apoE is involved in the tonic inhibition of steroidogenesis and adrenal cortical activity. These data are consistent with the inverse relationship between the levels of apoE mRNA and adrenal steroidogenesis (Prack et al., 1991, supra; and Nicosia et al., 1992, supra). The above results also demonstrate that the ApoE knockout mice are suitable animal models of anxiolytic activity testing of candidate anxiolytic compounds and to evaluate whether drugs enhance or inhibit ApoE3 or ApoE4-like effects on the HPA axis and emotional responses.

It is evident from the above results and discussion that the subject invention provides an important new method for the treatment of anxiety, as well as screening methods for identifying anxiolytic agents. In addition, the subject invention provides for an important new way to modulate adrenal steroidogenesis and the HPA axis. As such, the subject invention provides for a new way to treat a variety of conditions associated with HPA axis dysregulation. As such, the subject invention represents an significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of screening a compound for anxiolytic activity, said method comprising:
    (a) administering said compound to an Apolipoprotein $e^{-/-}$ knockout animal model of anxiety;
    (b) observing the effect of said compound on said Apolipoprotein $e^{-/-}$ knockout animal model; and
    (c) relating the observed effect of said compound on said Apolipoprotein $e^{-/-}$ knockout animal model of anxiety to the anxiolytic activity of said compound.

2. The method according to claim 1, wherein said Apolipoprotein $e^{-/-}$ knockout animal model is a mammal.

3. The method according to claim 2, wherein said mammal is a mouse.

4. The method according to claim 1, wherein said Apolipoprotein $e^{-/-}$ knockout animal model expresses Apolipoprotein E4.

5. The method according to claim 1, wherein said animal model is a male.

6. The method according to claim 4, wherein said Apolipoprotein E4 is not expressed in the adrenal gland of said Apolipoprotein $e^{-/-}$ knockout animal model.

7. The method according to claim 6, wherein said Apolipoprotein $e^{-/-}$ knockout animal model is a mammal.

8. The method according to claim 7, wherein said mammal is a mouse.

9. The method according to claim 6, wherein said animal model is a male.

10. A method of screening a compound for anxiolytic activity, said method comprising:
    (a) administering said compound to an Apolipoprotein $e^{-/-}$ knockout animal model wherein said animal model is transgenic for apolipoprotein E4 (apoE4) and wherein said animal model does not express Apolipoprotein E4 in the adrenal gland of said animal model;
    (b) observing the effect of said compound on said animal model; and
    (c) relating the observed effect of said compound on said animal model to the anxiolytic activity of said compound.

11. The method according to claim 10, wherein said animal model is a mammal.

12. The method according to claim 11, wherein said mammal is a mouse.

13. The method according to claim 12, wherein said animal model is a male.

* * * * *